(12) United States Patent
Kodama et al.

(10) Patent No.: US 8,697,601 B2
(45) Date of Patent: Apr. 15, 2014

(54) REWRITABLE RECORDING MATERIAL

(71) Applicant: Nippon Soda Co., Ltd., Tokyo (JP)

(72) Inventors: Satoshi Kodama, Ichihara (JP); Hiroshi Fujii, Ichihara (JP); Tadashi Kawakami, Ichihara (JP)

(73) Assignee: Nippon Soda Co., Ltd., Tokyo (JP)

( * ) Notice: Subject to any disclaimer, the term of this patent is extended or adjusted under 35 U.S.C. 154(b) by 0 days.

(21) Appl. No.: 13/891,703

(22) Filed: May 10, 2013

(65) Prior Publication Data

US 2013/0244873 A1    Sep. 19, 2013

Related U.S. Application Data

(63) Continuation of application No. 13/138,302, filed as application No. PCT/JP2010/000570 on Feb. 1, 2010, now abandoned.

(30) Foreign Application Priority Data

Feb. 3, 2009 (JP) ................... 2009-022195
Jul. 3, 2009 (JP) ................... 2009-158763

(51) Int. Cl.
*B41M 5/333* (2006.01)

(52) U.S. Cl.
USPC .......................................... 503/201; 503/216

(58) Field of Classification Search
USPC .................................. 503/200–226
See application file for complete search history.

(56) References Cited

U.S. PATENT DOCUMENTS 3,158,610 A    11/1964    Buell

FOREIGN PATENT DOCUMENTS

| EP | 0 374 048 A1 | 6/1990 |
|---|---|---|
| GB | 2 056 103 A | 3/1981 |
| JP | 56-027132 A | 3/1981 |
| JP | 60-193691 A | 10/1985 |
| JP | 61-237684 A | 10/1986 |
| JP | 63-173684 A | 7/1988 |
| JP | 02-153789 A | 6/1990 |
| JP | 05-058894 A | 3/1993 |
| JP | 06-171225 A | 6/1994 |
| JP | 08-301838 A | 11/1996 |
| JP | 09-295458 A | 11/1997 |
| JP | 10-067726 A | 3/1998 |
| JP | 2003-305959 A | 10/2003 |
| JP | 2005-001127 A | 1/2005 |
| JP | 2005-518371 A | 6/2005 |
| WO | WO 03/049702 A2 | 6/2003 |

OTHER PUBLICATIONS

Furuya et al., "Improvement of Coloring/decoloring Characteristics for Thermal Rewritable Recording Media Using Leuco Dye," Ricoh Technical Report No. 25, Nov. 1999, 6-14, English abstract on first page.

*Primary Examiner* — Bruce H Hess

(74) *Attorney, Agent, or Firm* — Foley & Lardner LLP

(57) ABSTRACT

A rewritable recording material can be provided which contains at least one kind of phenolic compounds represented by formula (I) and which is capable of stably repeating coloring and discoloring for a long period of time as well as exerting superior storage properties such as heat resistance and moisture and heat resistance of the colored image and light resistance of the background. Also provided are a composition for forming a rewritable color-forming layer which is capable of forming a color-forming layer of the recording material, and a composition of a color-developing agent for a rewritable recording material.

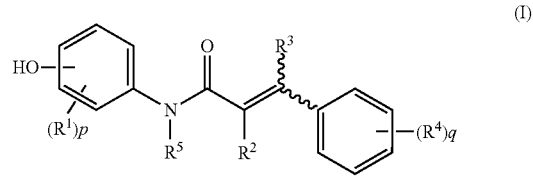

(I)

2 Claims, No Drawings

REWRITABLE RECORDING MATERIAL

CROSS-REFERENCE TO RELATED APPLICATIONS

The present application is a Continuation of U.S. application Ser. No. 13/138,302, filed Feb. 1, 2010, which claims priority to Japanese Patent Application Nos. 2009-22195 and 2009-158763 respectively filed on Feb. 3, 2009 and Jul. 3, 2009, the entire contents of which are hereby incorporated by reference.

TECHNICAL FIELD

The present invention relates to a rewritable recording material capable of forming and erasing the colored image.

BACKGROUND ART

Recording materials that utilize color formation resulted by reaction of a color-forming compound and a color-developing agent makes it possible to carry out recording in a short time with a relatively simple device without conducting cumbersome treatments such as developing/fixing. Such recording materials are thus widely used for thermal recording papers used for output recording such as for a facsimile and a printer.

On the other hand, there is proposed a so-called rewritable recording material that can form and erase the colored image on a color-forming layer in a thermally reversible manner.

In a rewritable recording material, when temperature of a composition which is initially in a discolored state is raised, color-formation takes place at a particular temperature and the composition evolves into a colored state. When cooled rapidly from the colored state, the composition can be cooled to room temperature while retaining the colored state, which colored state is then fixed. On the other hand, when cooled slowly from the colored state, discoloring occurs in the course of temperature reduction so that a discolored state same as the initial state or a relatively discolored state is formed.

Further, when temperature of the composition fixed at a colored state is raised again, discoloring occurs at temperature lower than the color-formation temperature. When temperature is decreased from the temperature at which such discoloring occurred, the state is reverted to a discolored state same as the initial state. Use as a rewritable recording material is enabled by thus controlling colored and discolored states.

Conventionally, color-developing agents mainly containing a long-chain aliphatic hydrocarbon group has been proposed as a color-developing agent used for a rewritable recording material as mentioned above. Such compounds make it possible to erase an image by formation of an intermolecular interaction caused by the long-chain aliphatic hydrocarbon group (see Patent Documents 1-4, Non-patent Document 1).

Further, as a color-developing agent used for a rewritable recording material, compounds not containing a long-chain aliphatic hydrocarbon group have been proposed (see Patent Documents 5-7). However, rewritable recording materials using these have not yet been established as practical recording materials due to the drawbacks in compatibility of coloring and discoloring properties and in stability with regard to the color optical density or the repeatability.

[Patent Document 1] Japanese Unexamined Patent Application Publication No. 8-301838

[Patent Document 2] Japanese Unexamined Patent Application Publication No. 9-295458

[Patent Document 3] Japanese Unexamined Patent Application Publication No. 10-67726

[Patent Document 4] Japanese Unexamined Patent Application Publication No. 2005-1127

[Patent Document 5] Japanese Unexamined Patent Application Publication No. 60-193691

[Patent Document 6] Japanese Unexamined Patent Application Publication No. 61-237684

[Patent Document 7] Japanese Unexamined Patent Application Publication No. 63-173684

[Non-patent Document 1] Ricoh Tech Report, No. 25 (1999)

SUMMARY OF THE INVENTION

Object to be Solved by the Invention

The object of the present invention is to provide a rewritable recording material which is capable of stably repeating coloring and discoloring for a long period of time and has a superior heat resistance of the colored image compared to conventional rewritable recording materials, a composition for forming a rewritable color-forming layer which is capable of forming a color-forming layer of the recording material, and a composition of a color-developing agent for a rewritable recording material.

Means to Solve the Object

Discoloring of the image in a rewritable recording material is caused by that a compound for color-developing agent is crystallized and undergoes phase separation from a color-forming compound as a result of re-heating the colored part.

The present inventors have keenly studied the compounds represented by formula (I) and have found that the compounds effectively undergo crystallization and phase separation so as to activate rewritability, and further that the compounds have a superior heat resistance of the colored image compared to conventional recording materials adopting a rewritable color-developing agent. The present invention is thus completed.

The present invention thus relates to: (1) a rewritable recording material comprising a color-forming layer on a substrate, wherein the color-forming layer contains a color-forming compound and at least one kind of phenolic compounds represented by formula (I)

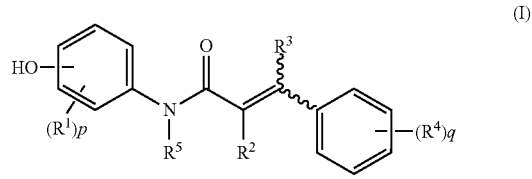

[wherein $R^1$ and $R^4$ each independently represent a hydrogen atom, hydroxy group, nitro group, halogen atom, $C_1$-$C_6$ alkyl group or $C_1$-$C_6$ alkoxy group; p represents 0 or an integer of 1 to 4; q represents 0 or an integer of 1 to 5; when p or q is 2 or more, $R^1$s and $R^4$s may be the same or different; $R^2$ and $R^3$ each independently represent a hydrogen atom or $C_1$-$C_6$ alkyl group; and $R^5$ represents a hydrogen atom, $C_1$-$C_6$ alkyl group, optionally substituted phenyl group, or optionally substituted benzyl group]; and (2) the rewritable recording material according to (1), wherein the substrate is a paper, synthetic resin film or synthetic resin sheet.

The present invention further relates to: (3) a composition for forming a rewritable color-forming layer, wherein the composition contains at least one kind of phenolic compounds represented by formula (I)

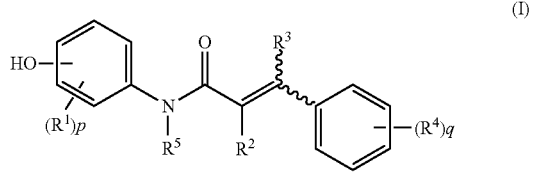

[wherein $R^1$ and $R^4$ each independently represent a hydrogen atom, hydroxy group, nitro group, halogen atom, $C_1$-$C_6$ alkyl group or $C_1$-$C_6$ alkoxy group; p represents 0 or an integer of 1 to 4; q represents 0 or an integer of 1 to 5; when p or q is 2 or more, $R^1$s and $R^4$s may be the same or different; $R^2$ and $R^3$ each independently represent a hydrogen atom or $C_1$-$C_6$ alkyl group; and $R^5$ represents a hydrogen atom, $C_1$-$C_6$ alkyl group, optionally substituted phenyl group, or optionally substituted benzyl group]; and (4) the composition for forming a rewritable color-forming layer according to (3), wherein the composition contains a color-forming compound and at least one kind of phenolic compounds represented by formula (I).

The present invention still further relates to (5) a composition of a color-developing agent for a rewritable recording material, wherein the composition comprises at least one kind of phenolic compounds represented by formula (I)

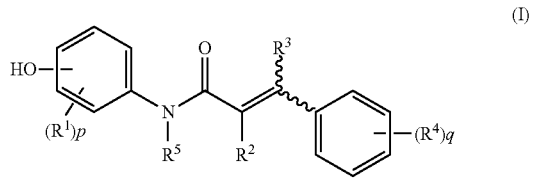

[wherein $R^1$ and $R^4$ each independently represent a hydrogen atom, hydroxy group, nitro group, halogen atom, $C_1$-$C_6$ alkyl group or $C_1$-$C_6$ alkoxy group; p represents 0 or an integer of 1 to 4; q represents 0 or an integer of 1 to 5; when p or q is 2 or more, $R^1$s and $R^4$s may be the same or different; $R^2$ and $R^3$ each independently represent a hydrogen atom or $C_1$-$C_6$ alkyl group; and $R^5$ represents a hydrogen atom, $C_1$-$C_6$ alkyl group, optionally substituted phenyl group, or optionally substituted benzyl group].

Effect of the Invention

According to the present invention, a rewritable recording material which is capable of stably repeating coloring and discoloring for a long period of time and which has a superior storage properties such as heat resistance and moisture and heat resistance of the colored image and light resistance of the background compared to conventional rewritable recording materials can be provided. Also provided is a composition for forming a rewritable color-forming layer which is capable of forming a color-forming layer of the recording material, and a composition of a color-developing agent for a rewritable recording material.

Mode of Carrying out the Invention (Rewritable Recording Material)

A rewritable recording material of the present invention is not particularly limited as long as it is a recording material comprising a color-forming layer on a substrate, wherein the color-forming layer contains a color-forming compound and at least one kind of phenolic compounds represented by formula (I)

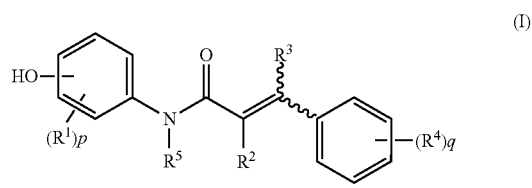

[wherein $R^1$ and $R^4$ each independently represent a hydrogen atom, hydroxy group, nitro group, halogen atom, $C_1$-$C_6$ alkyl group or $C_1$-$C_6$ alkoxy group; p represents 0 or an integer of 1 to 4; q represents 0 or an integer of 1 to 5; when p or q is 2 or more, $R^1$s and $R^4$s may be the same or different; $R^2$ and $R^3$ each independently represent a hydrogen atom or $C_1$-$C_6$ alkyl group; and $R^5$ represents a hydrogen atom, $C_1$-$C_6$ alkyl group, optionally substituted phenyl group, or optionally substituted benzyl group]. The color-forming layer can be formed by using a composition for forming a rewritable color-forming layer described below. The color-forming layer of the present invention is not particularly limited as long as it is a layer containing a color-forming compound and color-developing agent. The color-forming layer may be a layer containing a color-forming compound and a color-developing agent in a mixed state or may be multiple layers respectively containing a color-forming compound and a color-developing agent in separate layers.

A rewritable recording material of the present invention allows stable coloring and discoloring repeatedly for a long period of time and is superior in storage stability, especially heat resistance, of the colored image compared to conventional rewritable recording materials.

(Method for Producing a Phenolic Compound Represented by Formula (I))

A compound represented by formula (I) in the present invention can be obtained by reacting a compound represented by formula (II)

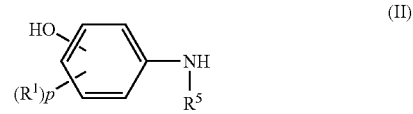

with a compound represented by formula (III)

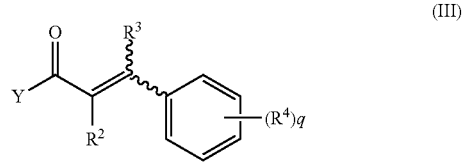

in an organic solvent such as acetonitrile and in the presence of a base such as pyridine. Here, $R^1$, $R^2$, $R^3$, $R^4$, $R^5$, p and q in formulae (II) and (III) have the same meaning as defined for formula (I), and Y represents a halogen atom such as a chlorine atom and bromine atom.

A compound represented by formula (I) has geometric isomers as shown below. There are cases where either type of geometric isomer is obtained or where a mixture of geometric isomers is obtained depending on the reaction conditions and purification methods. All of these geometric isomers are encompassed in the scope of the present invention.

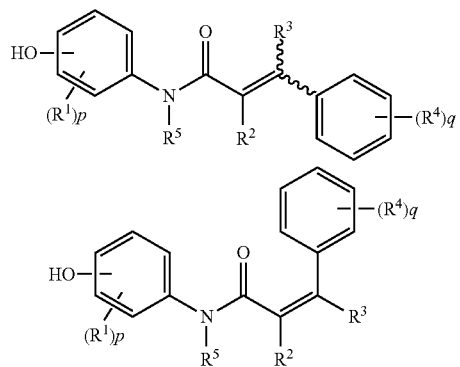

(Phenolic Compound Represented by Formula (I))

A phenolic compound represented by formula (I) is explained below.

In formula (I), $R^1$ and $R^4$ are each independently exemplified by a hydrogen atom; hydroxy group; nitro group; a halogen atom such as a fluorine atom, chlorine atom, bromine atom and iodine atom; a $C_1$-$C_6$ alkyl group such as a methyl group, ethyl group, n-propyl group, isopropyl group, n-butyl group, sec-butyl group, t-butyl group, n-pentyl group, isopentyl group, neopentyl group, t-pentyl group, n-hexyl group, isohexyl group, 1-methylpentyl group and 2-methylpentyl group, preferably a $C_1$-$C_4$ alkyl group; and a $C_1$-$C_6$ alkoxy group such as a methoxy group, ethoxy group, n-propoxy group, isopropoxy group, n-butoxy group, sec-butoxy group and t-butoxy group, preferably a $C_1$-$C_4$ alkoxy group. As $R^1$ and $R^4$, a hydrogen atom, methyl group and methoxy group are particularly preferred.

$R^2$ and $R^3$ are each independently exemplified by a hydrogen atom; and a $C_1$-$C_6$ alkyl group such as a methyl group, ethyl group, n-propyl group, isopropyl group, n-butyl group, sec-butyl group, t-butyl group, n-pentyl group, isopentyl group, neopentyl group, t-pentyl group, n-hexyl group, isohexyl group, 1-methylpentyl group and 2-methylpentyl group, preferably a $C_1$-$C_4$ alkyl group. As $R^2$ and $R^3$, a hydrogen atom and methyl group are particularly preferred.

$R^5$ is exemplified by a hydrogen atom; a $C_1$-$C_6$ alkyl group such as a methyl group, ethyl group, n-propyl group, isopropyl group, n-butyl group, sec-butyl group, t-butyl group, n-pentyl group, isopentyl group, neopentyl group, t-pentyl group, n-hexyl group, isohexyl group, 1-methylpentyl group and 2-methylpentyl group, preferably a $C_1$-$C_4$ alkyl group; an optionally substituted phenyl group; and an optionally substituted benzyl group. As $R^5$, a hydrogen atom is particularly preferred.

The examples of the above substituent include a hydroxy group; a halogen atom such as a fluorine atom, chlorine atom, bromine atom and iodine atom; a $C_1$-$C_6$ alkyl group such as a methyl group, ethyl group, n-propyl group, isopropyl group, n-butyl group, sec-butyl group, t-butyl group, n-pentyl group, isopentyl group, neopentyl group, t-pentyl group, n-hexyl group, isohexyl group, 1-methylpentyl group and 2-methylpentyl group; and a $C_1$-$C_6$ alkoxy group such as a methoxy group, ethoxy group, n-propoxy group, isopropoxy group, n-butoxy group, sec-butoxy group and t-butoxy group.

Specific examples of a phenolic compound represented by formula (I) are shown in Table 1.

TABLE 1

| No | OH, ($R^1$) p 2- | 3- | 4- | 5- | 6- | $R^5$ | $R^2$ | $R^3$ | ($R^4$) q 2- | 3- | 4- | 5- | 6- | mp |
|---|---|---|---|---|---|---|---|---|---|---|---|---|---|---|
| 1 | OH | H | H | H | H | H | H | H | H | H | H | H | H | 166-188 |
| 2 | OH | H | H | H | H | Ph | H | H | H | H | H | H | H | |
| 3 | OH | H | H | H | H | H | $CH_3$ | H | H | H | H | H | H | |
| 4 | OH | H | H | H | H | H | H | $CH_3$ | H | H | H | H | H | |
| 5 | OH | H | H | H | H | H | $CH_3$ | $CH_3$ | H | H | H | H | H | |
| 6 | OH | H | H | H | H | H | H | Ph | H | H | H | H | H | |
| 7 | OH | H | H | H | H | H | H | H | OH | H | H | H | H | |
| 8 | OH | H | H | H | H | H | $CH_3$ | H | OH | H | H | H | H | |
| 9 | OH | H | H | H | H | H | H | $CH_3$ | OH | H | H | H | H | |
| 10 | OH | H | H | H | H | H | $CH_3$ | $CH_3$ | OH | H | H | H | H | |
| 11 | OH | H | H | H | H | H | H | H | H | OH | H | H | H | |
| 12 | OH | H | H | H | H | Ph | H | H | H | OH | H | H | H | |
| 13 | OH | H | H | H | H | H | $CH_3$ | H | H | OH | H | H | H | |
| 14 | OH | H | H | H | H | Ph | H | H | H | H | OH | H | H | |
| 15 | OH | H | H | H | H | H | $CH_3$ | H | H | H | OH | H | H | |
| 16 | OH | H | H | H | H | H | $CH_3$ | $CH_3$ | H | H | OH | H | H | |
| 17 | OH | H | OH | H | H | H | H | H | H | H | H | H | H | |
| 18 | OH | H | $CH_3$ | H | H | H | H | H | H | H | H | H | H | |
| 19 | OH | H | H | $CH_3$ | H | H | H | H | H | H | H | H | H | |
| 20 | OH | H | H | H | $CH_3$ | H | H | H | H | H | H | H | H | |
| 21 | OH | H | $OCH_3$ | H | H | H | H | H | H | H | H | H | H | |
| 22 | OH | H | H | Cl | H | H | H | H | H | H | H | H | H | |
| 23 | OH | H | $NO_2$ | H | H | H | H | H | H | H | H | H | H | |
| 24 | OH | H | H | $NO_2$ | H | H | H | H | H | H | H | H | H | |
| 25 | OH | H | H | H | $NO_2$ | H | H | H | H | H | H | H | H | |
| 26 | OH | H | H | H | H | $CH_3$ | H | H | H | H | OH | H | H | |
| 27 | OH | H | H | H | H | $CH_2Ph$ | H | H | H | H | OH | H | H | |
| 28 | OH | H | H | H | H | 4-$CH_3$—Ph | H | H | H | H | OH | H | H | |
| 29 | OH | H | H | H | H | H | H | H | $CH_3$ | H | H | H | H | 212-213 |
| 30 | OH | H | H | H | H | H | H | H | H | $CH_3$ | H | H | H | 175-177 |
| 31 | OH | H | H | H | H | H | H | H | H | H | $CH_3$ | H | H | 202-204 |
| 32 | OH | H | H | H | H | H | H | H | F | H | H | H | H | |

TABLE 1-continued

| | OH, (R¹) p | | | | | | | | (R⁴) q | | | | | |
|---|---|---|---|---|---|---|---|---|---|---|---|---|---|---|
| No | 2- | 3- | 4- | 5- | 6- | R⁵ | R² | R³ | 2- | 3- | 4- | 5- | 6- | mp |
| 33 | OH | H | H | H | H | H | H | H | H | F | H | H | H | |
| 34 | OH | H | H | H | H | H | H | H | H | H | F | H | H | |
| 35 | OH | H | H | H | H | H | H | H | Cl | H | H | H | H | |
| 36 | OH | H | H | H | H | H | H | H | H | Cl | H | H | H | |
| 37 | OH | H | H | H | H | H | H | H | H | H | Cl | H | H | |
| 38 | OH | H | H | H | H | H | H | H | Br | H | H | H | H | |
| 39 | OH | H | H | H | H | H | H | H | H | Br | H | H | H | |
| 40 | OH | H | H | H | H | H | H | H | H | H | Br | H | H | |
| 41 | OH | H | H | H | H | H | H | H | I | H | H | H | H | |
| 42 | OH | H | H | H | H | H | H | H | H | I | H | H | H | |
| 43 | OH | H | H | H | H | H | H | H | H | H | I | H | H | |
| 44 | OH | H | H | H | H | H | H | H | NO₂ | H | H | H | H | |
| 45 | OH | H | H | H | H | H | H | H | H | NO₂ | H | H | H | |
| 46 | OH | H | H | H | H | H | H | H | H | H | NO₂ | H | H | |
| 47 | OH | H | H | H | H | H | H | H | OCH₃ | H | H | H | H | |
| 48 | OH | H | H | H | H | H | H | H | H | OCH₃ | H | H | H | |
| 49 | OH | H | H | H | H | H | H | H | H | H | OCH₃ | H | H | |
| 50 | OH | H | H | H | H | H | H | H | OCH₃ | OCH₃ | H | H | H | 196-197 |
| 51 | OH | H | H | H | H | H | H | H | OCH₃ | H | H | OCH₃ | H | |
| 52 | OH | H | H | H | H | H | H | H | H | OCH₃ | OCH₃ | H | H | 137-138 |
| 53 | OH | H | H | H | H | H | H | H | OCH₃ | OCH₃ | OCH₃ | H | H | |
| 54 | OH | H | H | H | H | H | H | H | H | OCH₃ | OCH₃ | OCH₃ | H | 208-209 |
| 55 | OH | H | H | H | H | H | H | H | H | H | Ph | H | H | |
| 56 | OH | H | H | H | H | H | H | H | H | OH | OH | H | H | |
| 57 | OH | H | H | H | H | H | H | H | H | OH | OCH₃ | H | H | |
| 58 | OH | H | H | H | H | H | H | H | H | Cl | Cl | H | H | |
| 59 | OH | H | H | H | H | H | H | H | Cl | H | Cl | H | H | |
| 60 | OH | H | H | H | H | H | H | H | Cl | H | H | NO₂ | H | |
| 61 | OH | H | H | H | H | H | H | H | H | NO₂ | Cl | H | H | |
| 62 | H | OH | H | H | H | H | H | H | H | H | H | H | H | 224-225 |
| 63 | H | OH | H | H | H | Ph | H | H | H | H | H | H | H | |
| 64 | H | OH | H | H | H | H | CH₃ | H | H | H | H | H | H | |
| 65 | H | OH | H | H | H | H | H | CH₃ | H | H | H | H | H | 203-204 |
| 66 | H | OH | H | H | H | H | CH₃ | CH₃ | H | H | H | H | H | |
| 67 | H | OH | H | H | H | H | H | Ph | H | H | H | H | H | 152-154 |
| 68 | H | OH | H | H | H | H | H | H | OH | H | H | H | H | |
| 69 | H | OH | H | H | H | Ph | H | H | OH | H | H | H | H | 126-127 |
| 70 | H | OH | H | H | H | H | CH₃ | H | OH | H | H | H | H | |
| 71 | H | OH | H | H | H | H | CH₃ | CH₃ | OH | H | H | H | H | |
| 72 | H | OH | H | H | H | H | H | H | H | OH | H | H | H | |
| 73 | H | OH | H | H | H | Ph | H | H | H | OH | H | H | H | |
| 74 | H | OH | H | H | H | H | CH₃ | H | H | OH | H | H | H | |
| 75 | H | OH | H | H | H | Ph | H | H | H | H | OH | H | H | |
| 76 | H | OH | H | H | H | H | CH₃ | H | H | H | OH | H | H | |
| 77 | H | OH | H | H | H | H | CH₃ | CH₃ | H | H | OH | H | H | |
| 78 | H | OH | H | H | H | CH₃ | H | H | H | H | OH | H | H | |
| 79 | H | OH | H | H | H | CH₂Ph | H | H | H | H | OH | H | H | |
| 80 | H | OH | H | H | H | 4-CH₃—Ph | H | H | H | H | OH | H | H | |
| 81 | H | OH | H | H | H | H | H | H | CH₃ | H | H | H | H | 199-200 |
| 82 | H | OH | H | H | H | H | H | H | H | CH₃ | H | H | H | 205-207 |
| 83 | H | OH | H | H | H | H | H | H | H | H | CH₃ | H | H | 223-225 |
| 84 | H | OH | H | H | H | H | H | H | F | H | H | H | H | |
| 85 | H | OH | H | H | H | H | H | H | H | F | H | H | H | |
| 86 | H | OH | H | H | H | H | H | H | H | H | F | H | H | 217-218 |
| 87 | H | OH | H | H | H | H | H | H | Cl | H | H | H | H | |
| 88 | H | OH | H | H | H | H | H | H | H | Cl | H | H | H | |
| 89 | H | OH | H | H | H | H | H | H | H | H | Cl | H | H | |
| 90 | H | OH | H | H | H | H | H | H | Br | H | H | H | H | |
| 91 | H | OH | H | H | H | H | H | H | H | Br | H | H | H | 189-190 |
| 92 | H | OH | H | H | H | H | H | H | H | H | Br | H | H | 222-223 |
| 93 | H | OH | H | H | H | H | H | H | I | H | H | H | H | |
| 94 | H | OH | H | H | H | H | H | H | H | I | H | H | H | |
| 95 | H | OH | H | H | H | H | H | H | H | H | I | H | H | |
| 96 | H | OH | H | H | H | H | H | H | NO₂ | H | H | H | H | |
| 97 | H | OH | H | H | H | H | H | H | H | NO₂ | H | H | H | |
| 98 | H | OH | H | H | H | H | H | H | H | H | NO₂ | H | H | |
| 99 | H | OH | H | H | H | H | H | H | OCH₃ | H | H | H | H | 185-186 |
| 100 | H | OH | H | H | H | H | H | H | H | OCH₃ | H | H | H | 161-162 |
| 101 | H | OH | H | H | H | H | H | H | H | H | OCH₃ | H | H | 218-219 |
| 102 | H | OH | H | H | H | H | H | H | OCH₃ | OCH₃ | H | H | H | 178-179 |
| 103 | H | OH | H | H | H | H | H | H | OCH₃ | H | H | OCH₃ | H | 170-171 |
| 104 | H | OH | H | H | H | H | H | H | H | OCH₃ | OCH₃ | H | H | 209-210 |
| 105 | H | OH | H | H | H | H | H | H | OCH₃ | OCH₃ | OCH₃ | H | H | |
| 106 | H | OH | H | H | H | H | H | H | H | OCH₃ | OCH₃ | OCH₃ | H | 245-246 |
| 107 | H | OH | H | H | H | H | H | H | H | H | Ph | H | H | 253-254 |
| 108 | H | H | OH | H | H | H | H | H | H | H | H | H | H | 209-212 |

TABLE 1-continued

| | OH, ($R^1$) p | | | | | | | | ($R^4$) q | | | | | |
|---|---|---|---|---|---|---|---|---|---|---|---|---|---|---|
| No | 2- | 3- | 4- | 5- | 6- | $R^5$ | $R^2$ | $R^3$ | 2- | 3- | 4- | 5- | 6- | mp |
| 109 | H | H | OH | H | H | Ph | H | H | H | H | H | H | H | |
| 110 | H | H | OH | H | H | H | $CH_3$ | H | H | H | H | H | H | |
| 111 | H | H | OH | H | H | H | H | $CH_3$ | H | H | H | H | H | |
| 112 | H | H | OH | H | H | H | $CH_3$ | $CH_3$ | H | H | H | H | H | |
| 113 | H | H | OH | H | H | H | H | Ph | H | H | H | H | H | 169-171 |
| 114 | H | H | OH | H | H | H | H | H | OH | H | H | H | H | |
| 115 | H | H | OH | H | H | Ph | H | H | OH | H | H | H | H | |
| 116 | H | H | OH | H | H | H | $CH_3$ | H | OH | H | H | H | H | |
| 117 | H | H | OH | H | H | H | $CH_3$ | $CH_3$ | OH | H | H | H | H | |
| 118 | H | H | OH | H | H | H | H | H | H | OH | H | H | H | |
| 119 | H | H | OH | H | H | Ph | H | H | H | OH | H | H | H | |
| 120 | H | H | OH | H | H | H | $CH_3$ | H | H | OH | H | H | H | |
| 121 | H | H | OH | H | H | Ph | H | H | H | H | OH | H | H | |
| 122 | H | H | OH | H | H | H | $CH_3$ | H | H | H | OH | H | H | |
| 123 | H | H | OH | H | H | H | $CH_3$ | $CH_3$ | H | H | OH | H | H | |
| 124 | H | H | OH | H | H | $CH_3$ | H | H | H | H | OH | H | H | |
| 125 | H | H | OH | H | H | $CH_2Ph$ | H | H | H | H | OH | H | H | |
| 126 | H | H | OH | H | H | 4-$CH_3$—Ph | H | H | H | H | OH | H | H | |
| 127 | H | H | OH | H | H | H | H | H | $CH_3$ | H | H | H | H | 192-194 |
| 128 | H | H | OH | H | H | H | H | H | H | $CH_3$ | H | H | H | 207-208 |
| 129 | H | H | OH | H | H | H | H | H | H | H | $CH_3$ | H | H | 196-198 |
| 130 | H | H | OH | H | H | H | H | H | F | H | H | H | H | |
| 131 | H | H | OH | H | H | H | H | H | H | F | H | H | H | |
| 132 | H | H | OH | H | H | H | H | H | H | H | F | H | H | |
| 133 | H | H | OH | H | H | H | H | H | Cl | H | H | H | H | |
| 134 | H | H | OH | H | H | H | H | H | H | Cl | H | H | H | |
| 135 | H | H | OH | H | H | H | H | H | H | H | Cl | H | H | |
| 136 | H | H | OH | H | H | H | H | H | Br | H | H | H | H | |
| 137 | H | H | OH | H | H | H | H | H | H | Br | H | H | H | |
| 138 | H | H | OH | H | H | H | H | H | H | H | Br | H | H | |
| 139 | H | H | OH | H | H | H | H | H | I | H | H | H | H | |
| 140 | H | H | OH | H | H | H | H | H | H | I | H | H | H | |
| 141 | H | H | OH | H | H | H | H | H | H | H | I | H | H | |
| 142 | H | H | OH | H | H | H | H | H | $NO_2$ | H | H | H | H | |
| 143 | H | H | OH | H | H | H | H | H | H | $NO_2$ | H | H | H | |
| 144 | H | H | OH | H | H | H | H | H | H | H | $NO_2$ | H | H | |
| 145 | H | H | OH | H | H | H | H | H | $OCH_3$ | H | H | H | H | |
| 146 | H | H | OH | H | H | H | H | H | H | $OCH_3$ | H | H | H | 183-184 |
| 147 | H | H | OH | H | H | H | H | H | H | H | $OCH_3$ | H | H | |
| 148 | H | H | OH | H | H | H | H | H | $OCH_3$ | $OCH_3$ | H | H | H | 208-210 |
| 149 | H | H | OH | H | H | H | H | H | $OCH_3$ | H | H | $OCH_3$ | H | 192-194 |
| 150 | H | H | OH | H | H | H | H | H | H | $OCH_3$ | $OCH_3$ | H | H | 223-224 |
| 151 | H | H | OH | H | H | H | H | H | $OCH_3$ | $OCH_3$ | $OCH_3$ | H | H | |
| 152 | H | H | OH | H | H | H | H | H | H | $OCH_3$ | $OCH_3$ | $OCH_3$ | H | 202-203 |
| 153 | H | H | OH | H | H | H | H | H | H | H | Ph | H | H | |

As a rewritable recording material of the present invention, compounds represented by compound Nos. 54, 62, 65, 82, 83, 101, 104, 108 and 128 are preferred among the compounds exemplified above. Particularly preferred is to use compounds represented by compound Nos. 62 and 82.

(Other Components of a Rewritable Recording Material)

Other than a compound represented by the above formula (I) and a color-forming compound, a rewritable recording material of the present invention may further contain as necessary one or more of the following: an image stabilizer, sensitizer, filler, dispersant, antioxidant, desensitizer, antiadhesive agent, defoamer, light stabilizer, fluorescent brightener, etc. These are respectively used in an amount of usually within a range of 0.1 to 15 parts by mass, preferably 1 to 10 parts by mass, relative to 1 part by mass of the color-forming compound.

These agents maybe contained in the color-forming layer, while they may be contained in any layer such as a protective layer when the recording material consists of a multilayer structure. Especially, when an overcoat layer or undercoat layer is provided on the upper part and/or the bottom part of the color-forming layer, such overcoat layer and undercoat layer may contain an antioxidant, light stabilizer, etc. Further, an antioxidant and alight stabilizer can be contained in these layers in such a manner as being encapsulated in a microcapsule according to need.

Examples of the color-forming compound to be used for a rewritable recording material of the present invention include: a leuco dye such as fluoran-based, phthalide-based, lactam-based, triphenylmethane-based, phenothiazine-based and spiropyran-based dyes. The color-forming compound, however, is not limited to these examples and any color-forming compound may be used as long as it forms color when contacted with a color-developing agent which is an acid substance. Further, although it is a matter of course to use these color-forming compounds singularly to produce a recording material of the color formed by the dye used, the color-forming compounds may also be used in combination of two or more kinds thereof. For example, it is possible to produce a recording material that produces a real black by using dyes developing three primary colors (red, blue, green) or black dyes in combination.

Examples of the color-forming compound include 3-diethylamino-6-methyl-7-anilinofluoran, 3-di(n-butyl)amino-6-methyl-7-anilinofluoran, 3-(N-methyl-N-cyclohexylamino)-6-methyl-7-anilinofluoran, 3-(N-ethyl-N- isobutylamino)-6-methyl-7-anilinofluoran, 3-(N-methyl-N-propylamino)-6-methyl-7-anilinofluoran, 3-(N-ethyl-N-isoamylamino)-6-methyl-7-anilinofluoran, 3-(N-ethyl-p-toluidino)-6-methyl-7-anilinofluoran, 3-diethylamino-7-(m-trifluoromethylanilino)fluoran, 3-di(n-pentyl)amino-6-methyl-7-anilinofluoran, 3-(N-ethyl-N-ethoxypropylamino)-6-methyl-7-anilinofluoran, 3-diethylamino-6-methyl-7-n-octylaminofluoran, 3-diethylamino-6-methyl-7-(m-methylanilino)fluoran, 3-diethylamino-6-methyl-7-(o,p-dimethylanilino)fluoran, 3-diethylamino-6-chloro-7-anilinofluoran, 3-diethylamino-7-(o-chloroanilino)fluoran, 3-dibutylamino-7-(o-chloroanilino)fluoran, 3-(N-ethyl-N-tetrahydrofurfurylamino)-6-methyl-7-anilinofluoran, 3-dibutylamino-7-(o-fluoroanilino)fluoran, 3-diethylamino-7-(o-fluoroanilino)fluoran, 2,4-dimethyl-6-[(4-dimethylamino)anilino]fluoran, 2-chloro-3-methyl-6-p(p-phenylaminophenyl)aminoanilinofluoran, 3,3-bis[1-(4-methoxyphenyl)-1-(4-dimethylaminophenyl)ethylene-2-yl]-4,5,6,7-tetrachlorophthalide, 3,6,6'-tris(dimethylamino) spiro[fluorene-9,3'-phthalide], 3,3-bis(p-dimethylaminophenyl)-6-dimethylaminophthalide, 10-benzoyl-3,7-bis (dimethylamino)phenothiazine, 3-(4-diethylamino-2-hexyloxyphenyl)-3-(1-ethyl-2-methyl-3-indolyl)-4-azaphthalide, 3-(4-diethylamino-2-methylphenyl)-3-(1-ethyl-2-methyl-3-indolyl)-4-azaphthalide, 3-(4-diethylamino-2-ethoxyphenyl)-3-(1-ethyl-2-methyl-3-indolyl)-4-azaphthalide, 3-(4-diethylamino-2-ethoxyphenyl)-3-(1-octyl-2-methyl-3-indolyl)-4-azaphthalide, 3-diethylamino-5-methyl-7-dibenzylaminofluoran, 3-diethylamino-7-dibenzylaminofluoran, 3-(N-ethyl-p-tolyl)amino-7-N-methylanilinofluoran, 3,3-bis(4-diethylamino-2-ethoxyphenyl)-4-azaphthalide, 3-[2,2-bis(1-ethyl-2-methylindole-3-yl)vinyl]-3-[4-(diethylamino)phenyl] isobenzofuran-1-one, 3,6,6'-tris(dimethylamino)spiro [fluorene-9,3'-phthalide], 2-[3,6-bis(diethylamino)-9-(o-chloroanilino)xanthyl]benzoic acid lactam, 3-diethylamino-7-chlorofluoran, 3,6-bis-(diethylamino)fluoran-γ-(4'-nitro)-anilinolactam, 3-diethylamino-benzo[a]fluoran, 3-(N-ethyl-N-isopentylamino)-benzo[a]fluoran, 2-methyl-6-(N-ethyl-N-p-tolylamino)fluoran, 3,3-bis(1-butyl-2-methyl-3-indolyl)phthalide, 3-diethylamino-6-methyl-7-chlorofluoran, 3-dibutylamino-6-methyl-7-bromofluoran, 3-cyclohexylamino-6-chlorofluoran, 3-diethylamino-6,8-dimethylfluoran, and 4,4'-isopropylidenedi(4-phenoxy)bis [4-(quinazoline-2-yl)-N,N-diethylaniline].

Preferred examples of the black dye include: 3-diethylamino-6-methyl-7-anilinofluoran, 3-di(n-butyl)amino-6-methyl-7-anilinofluoran, 3-(N-methyl-N-cyclohexylamino)-6-methyl-7-anilinofluoran, 3-(N-methyl-N-propylamino)-6-methyl-7-anilinofluoran, 3-(N-ethyl-N-isoamylamino)-6-methyl-7-anilinofluoran, 3-(N-ethyl-p-toluidino)-6-methyl-7-anilinofluoran, 3-diethylamino-7-(m-trifluoromethylanilino)fluoran, 3-di(n-pentyl)amino-6-methyl-7-anilinofluoran, 3-(N-ethyl-N-ethoxypropylamino)-6-methyl-7-anilinofluoran, 3-diethylamino-6-methyl-7-n-octylaminofluoran, 3-diethylamino-6-methyl-7-(m-methylanilino)fluoran, 3-diethylamino-6-chloro-7-anilinofluoran, 3-diethylamino-7-(o-chloroanilino)fluoran, 3-dibutylamino-7-(o-chloroanilino) fluoran, 3-(N-ethyl-N-tetrahydrofurfurylamino)-6-methyl-7-anilinofluoran, and 3-dibutylamino-7-(o-fluoroanilino) fluoran.

Especially preferred examples include: 3-diethylamino-6-methyl-7-anilinofluoran, 3-di(n-butyl)amino-6-methyl-7-anilinofluoran, 3-(N-ethyl-N-isoamylamino)-6-methyl-7-anilinofluoran, 3-(N-ethyl-p-toluidino)-6-methyl-7-anilinofluoran, and 3-di(n-pentyl)amino-6-methyl-7-anilinofluoran.

The near-infrared absorption dye can be exemplified by 3,3-bis[1-(4-methoxyphenyl)-1-(4-dimethylaminophenyl) ethylene-2-yl]-4,5,6,7-tetrachlorophthalide, and 3,6,6'-tris (dimethylamino)spiro[fluorene-9,3'-phthalide].

In addition, examples of the blue dye, green dye, red dye and yellow dye include: 3,3-bis(p-dimethylaminophenyl)-6-dimethylaminophthalide, 3-(4-diethylamino-2-ethoxyphenyl)-3-(1-ethyl-2-methyl-3-indolyl)-4-azaphthalide, 3-(4-diethylamino-2-ethoxyphenyl)-3-(1-octyl-2-methyl-3-indolyl)-4-azaphthalide, 3-diethylamino-7-dibenzylaminofluoran, 3-(N-ethyl-p-tolyl)amino-7-N-methylanilinofluoran, 3,3-bis(4-diethylamino-2-ethoxyphenyl)-4-azaphthalide, 3,6,6'-tris(dimethylamino)spiro[fluorene-9,3'-phthalide], 3-diethylamino-7-chlorofluoran, 3-diethylamino-benzo[a]fluoran, 3-diethylamino-6-methyl-7-chlorofluoran, 3-cyclohexylamino-6-chlorofluoran, 3-diethylamino-6,8-dimethylfluoran, and 4,4'-isopropylidenedi(4-phenoxy)bis [4-(quinazoline-2-yl)-N,N-diethylaniline].

Examples of the image storage stabilizer which can be used in combination with a composition of the present invention include the following and they may be used alone or in combination of two or more kinds thereof according to need: 1,1,3-tris(2-methyl-4-hydroxy-5-t-butylphenyl)butane, 1,1,3-tris(2-methyl-4-hydroxy-5-t-cyclohexylphenyl)butane, 4,4'-butylidenebis(6-t-butyl-3-methylphenol), 2,2'-methylenebis(6-t-butyl-4-methylphenol), 2,2'-methylenebis(6-t-butyl-4-ethylphenol), 4,4'-thiobis(6-t-butyl-3-methylphenol), 1,3,5-tris(2,6-dimethyl-4-t-butyl-3-hydroxybenzyl)isocyanurate, 1,3,5-tris[[3,5-bis(1,1-dimethylethyl)-4-hydroxyphenyl]methyl]-1,3,5-triazine-2,4,6(1H,3H,5H)-trione, 2-methyl-2-[[4-[[4-(phenylmethoxy)phenyl]sulfonyl]phenoxy] methyl]-oxirane, 2,4,8,10-(tetra(t-butyl)-6-hydroxy-12H-dibenzo[d,g][1,3,2]dioxaphosphocin-6-oxide sodium salt, 2,2-bis(4'-hydroxy-3',5'-dibromophenyl)propane, 4,4'-sulfonylbis(2,6-dibromophenol), 2-(2'-hydroxy-5'-methylphenyl) benzotriazole, 4-benzyloxy-4-(2-methylglycidyloxy)-diphenylsulfone, 4,4'-diglycidyloxydiphenylsulfone, 1,4-diglycidyloxybenzene, 4-(α-(hydroxymethyl)benzyloxy)-4'-hydroxydiphenylsulfone, and 2,2-methylenebis(4,6-tert-butylphenyl)phosphate.

Preferably exemplified are 1,1,3-tris(2-methyl-4-hydroxy-5-t-butylphenyl)butane, 1,1,3-tris(2-methyl-4-hydroxy-5-t-cyclohexylphenyl)butane, 4,4'-butylidenebis(6-t-butyl-3-methylphenol), 2,2'-methylenebis(4-ethyl-6-t-butylphenol), 1,3,5-tris(2,6-dimethyl-4-t-butyl-3-hydroxybenzyl)isocyanurate, 2-methyl-2-[[4-[[4-(phenylmethoxy)phenyl]sulfonyl]phenoxy]methyl]-oxirane, 4,4'-sulfonylbis(2,6-dibromophenol), and 2-(2'-hydroxy-5'-methylphenyl) benzotriazole.

Examples of the sensitizer include the following and they may be used alone or in combination of two or more kinds thereof according to need: a higher fatty acid amide such as stearic acid amide; benzamide; stearic acid anilide; acetoacetanilide; thioacetanilide; dibenzyl oxalate; di(4-methylbenzyl)oxalate; di(4-chlorobenzyl)oxalate; dimethyl phthalate; dimethyl terephthalate; dibenzyl terephthalate; dibenzyl isophthalate; bis(tert-butylphenol); diphenylsulfone and its derivative such as 4,4'-dimethoxydiphenylsulfone, 4,4'-diethoxydiphenylsulfone, 4,4'-dipropoxydiphenylsulfone, 4,4'-diisopropoxydiphenylsulfone, 4,4'-dibutoxydiphenylsulfone, 4,4'-diisobutoxydiphenylsulfone, 4,4'-dipentyloxydiphenylsulfone, 4,4'-dihexylphenylsulfone, 2,4'-dimethoxydiphenylsulfone, 2,4'-diethoxydiphenylsulfone, 2,4'-dipropoxydiphenylsulfone, 2,4'-diisopropoxydiphenylsulfone, 2,4'-dibutoxydiphenylsulfone, 2,4'-dipentyloxydiphenylsulfone, 2,4'-dihexyloxydiphenylsulfone; diethers of 4,4'-dihydroxydiphenylsulfone; diethers of 2,4'-dihydroxydiphenylsulfone; 1,2-bis(phenoxy)ethane; 1,2-bis(4-methylphenoxy) ethane; 1,2-bis(3-methylphenoxy)ethane; diphenylamine; carbazole; 2,3-di-m-tolylbutane; 4-benzylbiphenyl; 4,4'-dimethylbiphenyl; m-terphenyl; di-β-naphthylphenylenediamine; 1-hydroxy-2-naphthoic acid phenyl ester; 2-naphthylbenzyl ether; 4-methylphenyl-biphenylether; 1,2-bis(3,4-dimethylphenyl)ethane; 2,3,5,6-tetramethyl-4'-methyldiphenylmethane; 1,2-bis(phenoxymethyl) benzene; acrylic acid amide; diphenylsulfone; 4-acetylbiphenyl; and carbonic acid diphenyl.

Preferably exemplified are 2-naphthylbenzylether, m-terphenyl, p-benzylbiphenyl, benzyl oxalate, di(p-chlorobenzyl)oxalate, an equivalent mixture of benzyl oxalate and di(p-chlorobenzyl)oxalate, di(p-methylbenzyl)oxalate, an equivalent mixture of di(p-chlorobenzyl)oxalate and di(p-methylbenzyl)oxalate, 1-hydroxy-2-naphthoic acid phenyl ester, 1,2-diphenoxyethane, 1,2-di-(3-methylphenoxy) ethane, 1,2-bis(phenoxymethyl)benzene, dimethyl terephthalate, stearic acid amide, "amide AP-1" (a mixture of stearic acid amide and palmitic acid amide at 7:3), diphenylsulfone, and 4-acetylbiphenyl.

As a filler, silica, clay, kaolin, fired kaolin, talc, satin white, aluminum hydroxide, calcium carbonate, magnesium carbonate, zinc oxide, titanium oxide, barium sulfate, magnesium silicate, aluminum silicate and plastic pigment are exemplified. Preferably exemplified among these are a salt of alkaline earth metal, especially, a carbonate such as calcium carbonate and magnesium carbonate. The ratio of filler for use is 0.1 to 15 parts by mass, preferably 1 to 10 parts by mass relative to 1 part by mass of the color-forming compound. In addition, the fillers referred to above can be mixed for use.

Examples of the dispersant include polyvinyl alcohol; polyvinylalcohols having various saponification degrees and polymerization degrees such as acetoacetylated polyvinylalcohol, carboxy-denatured polyvinylalcohol and sulfonic acid-denatured polyvinylalcohol; polysodium acrylate; methylcellulose; carboxymethylcellulose; hydroxyethylcellulose; polyacrylamide; starch; sulfosuccinic acid esters such as dioctylsodium sulfosuccinate; dodecylbenzenesulfonic acid sodium; sodium salt of lauryl alcohol sulfate ester; and a fatty acid salt.

Examples of the antioxidant include 2,2'-methylenebis(4-methyl-6-tert-butylphenol), 2,2'-methylenebis(4-ethyl-6-tert-butylphenol), 4,4'-propylmethylenebis(3-methyl-6-tert-butylphenol), 4,4'-butylidenebis(3-methyl-6-tert-butylphenol), 4,4'-thiobis(2-tert-butyl-5-methylphenol), 1,1,3-tris(2-methyl-4-hydroxy-5-tert-butylphenol)butane, 4-[4-{1,1-bis(4-hydroxyphenyl)ethyl}-α,α'-dimethylbenzyl] phenol, 1,1,3-tris(2-methyl-4-hydroxy-5-cyclohexylphenyl) butane, 2,2'-methylenebis(6-tert-butyl-4-methylphenol), 2,2'-methylenebis(6-tert-butyl-4-ethylphenol), 4,4'-thiobis (6-tert-butyl-3-methyl-phenol, 1,3,5-tris((4-(1,1-dimethylethyl)-3-hydroxy-2,6-dimethylphenyl)methyl-1,3,5-triazine-2,4,6(1H,3H,5H)-trione, and 1,3,5-tris((3,5-bis(1,1-dimethylethyl)-4-hydroxyphenyl)methyl)-1,3,5-triazine-2,4,6(1H,3H,5H)-trione.

The desensitizer is exemplified by a fatty higher alcohol, polyethyleneglycol and guanidine derivative.

The antiadhesive agent is exemplified by stearic acid, zinc stearate, calcium stearate, carnauba wax, paraffin wax and ester wax.

Examples of the defoamer include those based on higher alcohol, fatty acid ester, oil, silicone, polyether, denatured hydrocarbon and paraffin.

Examples of the light stabilizer include: a salicylic acid-based ultraviolet absorber such as phenylsalicylate, p-tert-butylphenylsalicylate, and p-octylphenylsalicylate; a benzophenone-based ultraviolet absorber such as 2,4-dihydroxybenzophenone, 2-hydroxy-4-methoxybenzophenone, 2-hydroxy-4-benzyloxybenzophenone, 2-hydroxy-4-dodecyloxybenzophenone, 2,2'-dihydroxy-4-methoxybenzophenone, 2,2'-dihydroxy-4,4'-dimethoxybenzophenone, 2-hydroxy-4-methoxy-5-sulfobenzophenone, and bis(2-methoxy-4-hydroxy-5-benzoylphenyl)methane; a benzotriazole-based ultraviolet absorber such as 2-(2'-hydroxy-5'-methylphenyl)benzotriazole, 2-(2'-hydroxy-5'-tert-butylphenyl) benzotriazole, 2-(2'-hydroxy-3',5'-di-tert-butylphenyl) benzotriazole, 2-(2'-hydroxy-3-tert-butyl-5'-methylphenyl)-5-chloro-benzotriazole, 2-(2'-hydroxy-3',5'-di-tert-amylphenyl)benzotriazole, 2-(2'-hydroxy-3',5'-di-tert-butylphenyl)-5-chlorobenzotriazole, 2-(2'-hydroxy-5'-tert-butylphenyl)benzotriazole, 2-(2'-hydroxy-5'-(1",1",3",3"-tetramethylbutyl)phenyl)benzotriazole, 2-[2'-hydroxy-3'-(3",4",5",6"-tetrahydrophthalimidomethyl)-5'-methylphenyl]benzotriazole, 2-(2'-hydroxy-5'-tert-octylphenyl)benzotriazole, 2-[2'-hydroxy-3',5'-bis(α,α'-dimethylbenzyl)phenyl]-2H-benzotriazole, 2-(2'-hydroxy-3'-dodecyl-5'-methylphenyl)benzotriazole, 2-(2'-hydroxy-3'-undecyl-5'-methylphenyl)benzotriazole, 2-(2'-hydroxy-3'-tridecyl-5'-methylphenyl)benzotriazole, 2-(2'-hydroxy-3'-tetradecyl-5'-methylphenyl)benzotriazole, 2-(2'-hydroxy-3'-pentadecyl-5'-methylphenyl)benzotriazole, 2-(2'-hydroxy-3'-hexadecyl-5'-methylphenyl)benzotriazole, 2-[2'-hydroxy-4'-(2"-ethylhexyl)oxyphenyl]benzotriazole, 2-[2'-hydroxy-4'-(2"-ethylheptyl)oxyphenyl]benzotriazole, 2-[2'-hydroxy-4'-(2"-ethyloctyl)oxyphenyl]benzotriazole, 2-[2'-hydroxy-4'-(2"-propyloctyl)oxyphenyl]benzotriazole, 2-[2'-hydroxy-4'-(2"-propylheptyl)oxyphenyl]benzotriazole, 2-[2'-hydroxy-4'-(2"-propylhexyl)oxyphenyl]benzotriazole, 2-[2'-hydroxy-4'-(1"-ethylhexyl)oxyphenyl]benzotriazole, 2-[2'-hydroxy-4'-(1"-ethylheptyl)oxyphenyl]benzotriazole, 2-[2'-hydroxy-4'-(1"-ethyloctyl)oxyphenyl]benzotriazole, 2-[2'-hydroxy-4'-(1"-propyloctyl)oxyphenyl]benzotriazole, 2-[2'-hydroxy-4'-(2"-propylheptyl)oxyphenyl]benzotriazole, 2-[2'-hydroxy-4'-(2"-propylhexyl)oxyphenyl]benzotriazole, 2,2'-methylenebis[4-(1,1,3,3-tetramethylbutyl)-6-(2H-benzotriazole-2-yl)phenol, and a condensate of polyethyleneglycol and methyl-3-[3-tert-butyl-5-(2H-benzotriazole-2-yl)-4-hydroxyphenyl]propionate; a cyanoacrylate-based ultraviolet absorber such as 2'-ethylhexyl-2-cyano-3,3-diphenylacrylate, and ethyl-2-cyano-3,3-diphenylacrylate; a hindered amine-based ultraviolet absorber such as bis(2,2,6,6-tetramethyl-4-piperidyl)sebacate, succinic acid-bis(2,2,6,6-tetramethyl-4-piperidyl)ester, and 2-(3,5-di-tert-butyl)malonic acid-bis(1,2,2,6,6-pentamethyl-4-piperidyl)ester; and 1,8-dihydroxy-2-acetyl-3-methyl-6-methoxynaphthalene and its related compounds.

Examples of the fluorescent dye include 4,4'-bis[2-anilino-4-(hydroxyethyl)amino-1,3,5-triazinyl-6-amino]stilbene-2, 2'-disulfonic acid disodium salt, 4,4'-bis[2-anilino-4-bis(hydroxyethyl)amino-1,3,5-triazinyl-6-amino]stilbene-2,2'-disulfonic acid disodium salt, 4,4'-bis[2-methoxy-4-(hydroxyethyl)amino-1,3,5-triazinyl-6-amino]stilbene-2,2'-disulfonic acid disodium salt, 4,4'-bis[2-anilino-4-(hydroxypropyl)amino-1,3,5-triazinyl-6-amino]stilbene-2, 2'-disulfonic acid disodium salt, 4,4'-bis[2-m-sulfoanilino-4-bis(hydroxyethyl)amino-1,3,5-triazinyl-6-amino]stilbene-2, 2'-disulfonic acid disodium salt, 4-[2-p-sulfoanilino-4-bis (hydroxyethyl)amino-1,3,5-triazinyl-6-amino]-4'-[2-m- sulfoanilino-4-bis(hydroxyethyl)amino-1,3,5-triazinyl-6-amino]stilbene-2,2'-disulfonic acid tetrasodium salt, 4,4'-bis[2-p-sulfoanilino-4-bis(hydroxyethyl)amino-1,3,5-triazinyl-6-amino]stilbene-2,2'-disulfonic acid tetrasodium salt, 4,4'-bis[2-(2,5-disulfoanilino)-4-phenoxyamino-1,3,5-triazinyl-6-amino]stilbene-2,2'-disulfonic acid hexasodium salt, 4,4'-bis[2-(2,5-disulfoanilino)-4-(p-methoxycarbonylphenoxy)amino-1,3,5-triazinyl-6-amino]stilbene-2,2'-disulfonic acid hexasodium salt, 4,4'-bis[2-(p-sulfophenoxy)-4-bis(hydroxyethyl)amino-1,3,5-triazinyl-6-amino]stilbene-2,2'-disulfonic acid hexasodium salt, 4,4'-bis[2-(2,5-disulfoanilino)-4-formalinylamino-1,3,5-triazinyl-6-amino]stilbene-2,2'-disulfonic acid hexasodium salt, and 4,4'-bis[2-(2,5-disulfoanilino)-4-bis(hydroxyethyl)amino-1,3,5-triazinyl-6-amino]stilbene-2,2'-disulfonic acid hexasodium salt.

(Substrate of Rewritable Recording Material)

A substrate for a rewritable recording material of the present invention is preferably a substrate which can be used repeatedly, and the examples include paper, synthetic paper, synthetic resin film, synthetic resin sheet, non-woven fabric, recycled paper such as waste paper pulp. Particularly preferred among these are a synthetic resin film and synthetic resin sheet for their property of being less prone to deterioration and being continuously usable for a long period of time. Examples of the synthetic resin film and synthetic resin sheet include a film or sheet of such as polyethylene, polypropylene, polyvinyl chloride, polyvinylidene chloride, ethylene-vinyl acetate copolymer, ethylene-vinyl alcohol copolymer, polyethylene terephthalate, polybutylene terephthalate, polyethylene naphthalate, polymethylmethacrylate, polymethylacrylate, polyethylmethacrylate, polystyrene, cellulose triacetate, cellophane and polycarbonate.

(Constitution of a Composition for Forming a Rewritable Color-Forming Layer)

A composition for forming a rewritable color-forming layer of the present invention is not particularly limited as long as it contains a color-forming compound and a phenolic compound represented by formula (I). The composition may be a mixture of a color-forming compound and a phenolic compound represented by formula (I) or may be a combination of compositions(separate substances) that respectively contain a color-forming compound and a phenolic compound represented by formula (I). Further, a composition for forming a rewritable color-forming layer of the present invention may contain as necessary one or more of the following in addition to a compound represented by formula (I) : a color-forming compound, an image stabilizer, sensitizer, filler, dispersant, antioxidant, desensitizer, antiadhesive agent, defoamer, light stabilizer, fluorescent brightener, etc., details of which are described above.

Further, known color-developing agents for rewritable recording material may be used in combination other than a compound represented by formula (I). Following is the examples of the color-developing agent that can be used in combination.

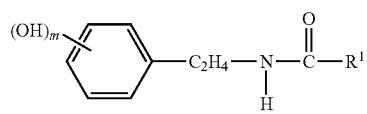

(wherein m represents an integer of 1 to 3, and $R^1$ represents an alkyl group with 20-30 carbons)

(Compounds described in Patent Document 4, Japanese Unexamined Patent Application Publication No. 2005-1127)

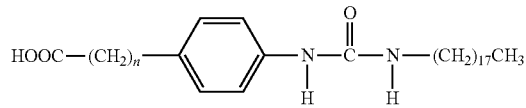

(wherein n represents an integer of 1 to 3)

(Compounds described in Patent Document 1, Japanese Unexamined Patent Application Publication No. 8-301838)

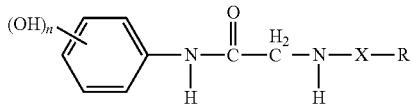

(wherein X represents a heteroatom-containing divalent group; R represents a hydrocarbon group having 8 or more carbons and optionally comprising a substituent; and n represents an integer of 1 to 3)

(Compounds described in Patent Document 2, Japanese Unexamined Patent Application Publication No. 9-295458)

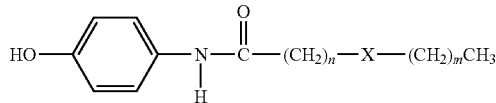

(wherein X represents a group shown by —NHCONH—, —NHCO—, —NHCOCONH—, —CONHNHCO— or —SO$_2$—; n represents an integer of 2 to 11; and m represents an integer of 6 to 21)

(Compounds described in Patent Document 3, Japanese Unexamined Patent Application Publication No. 10-67726)

Particularly preferred examples are the following compounds.

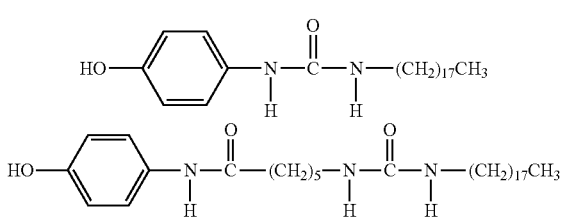

(Method for Producing and Using a Rewritable Recording Material)

A rewritable recording material of the present invention can be produced in a similar manner to methods for producing conventional recording materials. For example, a rewritable recording material can be produced as follows. Dispersion solutions are mixed and applied onto a substrate and dried, wherein the dispersion solutions are prepared by respectively dispersing microparticles of a color-forming compound and microparticles of a compound represented by formula (I) in the aqueous solutions comprising a water-soluble binder such as polyvinylalcohol and cellulose. Alternatively, a rewritable recording material of the present invention can also be produced by separately applying and drying respective dispersion solutions of a color-forming compound and a compound represented by formula (I) on a support. Ratio of a compound represented by formula (I) to be used relative to 1 part by mass of a color-forming compound is usually 0.1 to 15 parts by mass, preferably 1 to 10 parts by mass and more preferably 1.5 to 5 parts by mass.

Formation of a colored image by using a rewritable recording material of the present invention can be achieved by heating a rewritable recording material to the temperature equal to or higher than the color-forming temperature, followed by a rapid cooling. Specifically, when heated for a short time using such as a thermal head or laser beam, a recording material is heated locally, thereby undergoes immediate diffusion of the heat and rapid cooling, and the colored state can be fixed.

On the other hand, discoloring can be achieved either by heating a recording material to the temperature equal to or higher than the color-forming temperature with an appropriate heat source and cooling slowly, or by temporarily heating a recording material to the temperature somewhat lower than the color-forming temperature. When heated for a long period of time, temperature of the wide area of a recording material is raised. Then, upon halting the heating, the recording material is cooled slowly and discoloring occurs during the cooling process. As a heating method for the above case, a heating bar, heating roller, heating stamp and hot-air can be used, or the full width may be heated by heating for a long time using a thermal head or heating heater elements concurrently. A recording material can be heated to the discoloring temperature range by somewhat reducing the applied energy level from that of when recording takes place by, for example, controlling the voltage or the pulse width applied on a thermal head. With this method, recording and erasing can be done only with a thermal head, thereby enabling a so-called rewriting. As a matter of course, erasing can be performed by heating a recording material to a discoloring temperature range using a heating bar, heating roller, heating stamp, hot-air and the like.

The present invention is explained specifically in the following with reference to the Examples, but the technical scope of the present invention shall not be limited only to these exemplifications.

EXAMPLE

Example 1

(Production of a Thermal Paper)

| (a) Dispersion solution of a dye (solution A) | |
|---|---|
| 3-Di-n-butylamino-6-methyl-7-anilinofluoran | 16 parts |
| Aqueous solution of 10% polyvinylalcohol | 84 parts |
| (b) Dispersion solution of a color-developing agent (solution B) | |
| Compound No. 62 (see Table 1) | 16 parts |
| Aqueous solution of 10% polyvinylalcohol | 84 parts |
| (c) Dispersion solution of a sensitizer (solution C) | |
| Di(4-methylbenzyl)oxalate | 16 parts |
| Aqueous solution of 10% polyvinylalcohol | 84 parts |

| (d) Dispersion solution of a filler (solution D) | |
|---|---|
| Calcium carbonate | 27.8 parts |
| Aqueous solution of 10% polyvinylalcohol | 26.2 parts |
| Water | 71 parts |

First, mixtures of solutions A to D consisting of respective components were respectively ground well in a sand grinder to prepare the dispersion solutions of solutions A to D consisting of the respective components. A coating solution was prepared by mixing 1 part by mass of solution A, 2 parts by mass of solution B, 1 part by mass of solution C and 4 parts by mass of solution D. This coating solution was applied and dried on a white paper using a wire rod (Wire bar No. 12, product of Webster), followed by a calendering treatment to produce a thermal paper (coating amount was about 5.5 g/m$^2$ in terms of dry mass).

Example 2

A thermal paper was produced according to the method of Example 1, except that 1 part by mass of the following solution E was used in place of 1 part by mass of solution B of Example 1.

| (e) Dispersion solution of a color-developing agent (solution E) | |
|---|---|
| Compound No. 82 | 16 parts |
| Aqueoussolution of 10% polyvinyl alcohol | 84 parts |

Comparative Example 1

A thermal paper was produced according to the method of Example 1, except that 1 part by mass of the following solution F was used in place of 1 part by mass of solution B of Example 1.

| (f) Dispersion solution of a color-developing agent (solution F) | |
|---|---|
| Compound (A) (compound described in Non-patent Document 1) | 16 parts |
| Aqueous solution of 10% polyvinylalcohol | 84 parts |

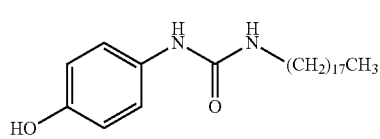

(A)

Comparative Example 2

A thermal paper was produced according to the method of Example 1, except that 1 part by mass of the following solution G was used in place of 1 part by mass of solution B of Example 1.

| (g) Dispersion solution of a color-developing agent (solution G) | |
|---|---|
| Compound (B) (compound described in Patent Document 3, Japanese Unexamined Patent Application Publication No. 10-67726) | 16 parts |
| Aqueous solution of 10% polyvinylalcohol | 84 parts |

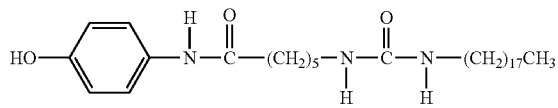

(B)

Comparative Example 3

A thermal paper was produced according to the method of Example 1, except that 1 part by mass of the following solution H was used in place of 1 part by mass of solution B of Example 1.

| (h) Dispersion solution of a color-developing agent (solution H) | |
|---|---|
| 4-hydroxy-4'-isopropoxydiphenylsulfone | 16 parts |
| Aqueous solution of 10% polyvinylalcohol | 84 parts |

Example 3

A thermal paper was produced according to the method of Example 1, except that 0.5 parts by mass of solution B and 0.5 parts by mass of solution G were used in place of 1 part by mass of solution B of Example 1.

Comparative Example 4

A thermal paper was produced according to the method of Example 1, except that 0.5 parts by mass of solution F and 0.5 parts by mass of solution G were used in place of 1 part by mass of solution B of Example 1.

Comparative Example 5

A thermal paper was produced according to the method of Example 1, except that 0.5 parts by mass of solution F and 0.5 parts by mass of solution H were used in place of 1 part by mass of solution B of Example 1.

Comparative Example 6

A thermal paper was produced according to the method of Example 1, except that 0.5 parts by mass of solution G and 0.5 parts by mass of solution H were used in place of 1 part by mass of solution B of Example 1.

(Test 1)

Thermal papers produced in Examples 1-3 and Comparative Examples 1-6 were subjected to saturated color formation under the condition of 0.72 mj per dot using a thermal printing tester (Model name: TH-PMH, product of Ohkura Electric Co., Ltd.). Then, density of the obtained image was determined using a Macbeth Reflection Densitometer (Model number: RD-918, filter used: #106, product of Macbeth Co., Ltd.). The results are shown in Table 2.

(Test 2)

The image parts obtained in Test 1 were heated for 5 sec at 120° C. using a heating stamp and determined using a Macbeth Reflection Densitometer (filter used: #106). The results are shown in Table 2.

(Test 3)

The samples in Test 2 were subjected to color formation again under the condition of 0.72 mj per dot using a thermal printing tester (Model name: TH-PMH, product of Ohkura Electric Co., Ltd.). Then, density of the obtained image was determined using a Macbeth Reflection Densitometer (filter used: #106). The results are shown in Table 2.

(Test 4: Heat Resistance of the Image)

Each of the test papers obtained in Test 1 was kept in a thermostat device (Product name: DK-400, product of Yamato Scientific Co., Ltd.) for 24 hours at 60° C. Optical density of the image after having been kept was determined using a Macbeth Reflection Densitometer (filter used: #106). The results are shown in Table 2.

(Test 5: Moisture and Heat Resistance of the Image)

Each of the test papers obtained in Test 1 was kept in a constant low temperature humidity chamber (Product name: THN050FA, product of ADVANTEC) for 24 hours at 40° C. and 90% conditions. Optical density of the image after having been kept was determined using a Macbeth Reflection Densitometer (filter used: #106). The results are shown in Table 2.

(Test 6: Background Light Resistance)

A part of each of the test papers produced was cut off and subjected to a light resistance test using a light resistance test device (Product name: UV Long-Life Fade Meter U48, product of Suga Test Instruments Co., Ltd.). Then, the background density after 8 hours was determined using a Macbeth Reflection Densitometer (filter used: #47). The results are shown in Table 2.

(Test 7: Dispersibility)

The dispersion solution of color-developing agent prepared in each of the Examples and Comparative Examples were ground in a sand grinder, and the time required to obtain a 50% volume average particle size of 0.90 μm or less was measured. The 50% volume average particle size was measured using a diffraction particle size analyzer (Product name: LA-920, product of HORIBA Ltd.). The results are shown in Table 2. The unit is minute.

(Contrast)

Coloring and discoloring were repeated for 15 times for the same image, in a similar manner to Tests 1-3. Then, the colored part at the colored state at the 15th run and the discolored part at the discolored state at the 15th run were compared. When density of the discolored part is less than 30% relative to density of the colored part so that the contrast of the colored and discolored parts is good, the contrast is evaluated as ◯; when density of the discolored part is 30% or more and less than 80% relative to density of the colored part so that the contrast is insufficient, the contrast is evaluated as Δ; and when density of the discolored part is 80% or more relative to density of the colored part so that reversibility is not observed, the contrast is evaluated as X.

TABLE 2

| | Test 1 | Test 2 | Test 3 | Test 4 | Test 5 | Test 6 | Test 7 | Contrast |
|---|---|---|---|---|---|---|---|---|
| Example 1 | 1.07 | 0.20 | 1.23 | 1.22 | 1.17 | 0.15 | 60 | ○ |
| Example 2 | 1.16 | 0.16 | 1.14 | 1.21 | 1.17 | — | 25 | ○ |
| Comparative Ex. 1 | 1.28 | 0.12 | 1.02 | 0.20 | 0.33 | 0.28 | 320 | ○ |
| Comparative Ex. 2 | 0.74 | 0.11 | 0.79 | 0.29 | 0.59 | 0.25 | 380 | ○ |
| Comparative Ex. 3 | 1.35 | 1.33 | 1.32 | 1.41 | 1.40 | 0.28 | 70 | x |
| Example 3 | 1.25 | 0.29 | 1.26 | 1.19 | 1.19 | 0.19 | | |
| Comparative Ex. 4 | 1.01 | 0.25 | 1.04 | 0.36 | 1.29 | 0.30 | | |
| Comparative Ex. 5 | 1.33 | 1.36 | 1.34 | 1.29 | 1.28 | 0.30 | | |
| Comparative Ex. 6 | 1.27 | 1.26 | 1.27 | 1.27 | 0.74 | 0.27 | | |

It can be known from Tests 1 to 3 shown in Table 2 above that recording materials of the present invention have a good rewritability. At the same time, it can be known from Tests 4 to 6 that heat resistance and moisture and heat resistance of the colored image is remarkably superior and that light resistance of the background is also superior.

The invention claimed is:

1. A method of forming a colored image on a rewritable recording material, comprising
heating a rewritable recording material to the temperature equal to or higher than the color-forming temperature, followed by cooling the rewritable recording material at a rate sufficient to retain the colored image during the cooling step,
wherein the rewritable recording material comprises at least one phenolic compound represented by formula (I)

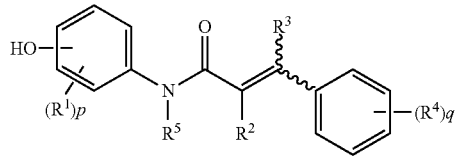

(I)

wherein $R^1$ and $R^4$ each independently represent a hydrogen atom, hydroxy group, nitro group, halogen atom, $C_1$-$C_4$ alkyl group or $C_1$-$C_4$ alkoxy group; p represents 0 or an integer of 1 to 4; q represents 0 or an integer of 1 to 5; When p or q is 2 or more, $R^1$s and $R^4$s may be the same or different; $R^2$ and $R^3$ each independently represent a hydrogen atom or $C_1$-$C_4$ alkyl group; and $R^5$ represents a hydrogen atom, $C_1$-$C_4$ alkyl group, optionally substituted phenyl group, or optionally substituted benzyl group.

2. A method of discoloring a colored image on a rewritable recording material, comprising
heating a rewritable recording material to the temperature equal to or higher than the color-forming temperature, followed by cooling the rewritable recording material at a rate sufficient to effect discoloring during the cooling step,
wherein the rewritable recording material comprises at least one phenolic compound represented by formula (I)

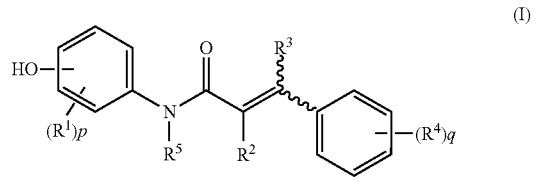

(I)

wherein $R^1$ and $R^4$ each independently represent a hydrogen atom, hydroxy group, nitro group, halogen atom, $C_1$-$C_4$ alkyl group or $C_1$-$C_4$ alkoxy group; p represents 0 or an integer of 1 to 4; q represents 0 or an integer of 1 to 5; when p or q is 2 or more, $R^1$s and $R^4$s may be the same or different; $R^2$ and $R^3$ each independently represent a hydrogen atom or $C_1$ alkyl group; and $R^5$ represents a hydrogen atom, $C_1$-$C_4$ alkyl group, optionally substituted phenyl group, or optionally substituted benzyl group.

* * * * *